(12) United States Patent
Kontschieder et al.

(10) Patent No.: US 10,083,233 B2
(45) Date of Patent: Sep. 25, 2018

(54) VIDEO PROCESSING FOR MOTOR TASK ANALYSIS

(71) Applicant: Microsoft Technology Licensing, LLC, Redmond, WA (US)

(72) Inventors: Peter Kontschieder, Cambridge (GB); Jonas Dorn, Reinach BL (CH); Darko Zikic, Cambridge (GB); Antonio Criminisi, Cambridge (GB)

(73) Assignee: Microsoft Technology Licensing, LLC, Redmond, WA (US)

( * ) Notice: Subject to any disclaimer, the term of this patent is extended or adjusted under 35 U.S.C. 154(b) by 0 days.

(21) Appl. No.: 14/536,660

(22) Filed: Nov. 9, 2014

(65) Prior Publication Data

US 2016/0071284 A1 Mar. 10, 2016

Related U.S. Application Data

(60) Provisional application No. 62/048,132, filed on Sep. 9, 2014.

(51) Int. Cl.
*G06K 9/00* (2006.01)
*G06F 17/30* (2006.01)
(Continued)

(52) U.S. Cl.
CPC .. *G06F 17/30784* (2013.01); *G06F 17/30887* (2013.01); *G06F 19/345* (2013.01);
(Continued)

(58) Field of Classification Search
CPC ........... G06K 9/00355; G06K 9/00375; G06K 2009/00738; G06K 9/00335;
(Continued)

(56) References Cited

U.S. PATENT DOCUMENTS 8,189,866 B1 * 5/2012 Gu .................... G06K 9/00335
348/169
8,213,678 B2 * 7/2012 Willmann ............ A61B 5/0064
382/103

(Continued)

FOREIGN PATENT DOCUMENTS

WO 2013027091 A1 2/2013
WO 2014113813 A1 7/2014

OTHER PUBLICATIONS

Martinez, Fabio, Antoine Manzanera, and Eduardo Romero. "A motion descriptor based on statistics of optical flow orientations for action classification in video-surveillance." In Multimedia and Signal Processing, pp. 267-274. Springer Berlin Heidelberg, 2012.*

(Continued)

*Primary Examiner* — Carol Wang
(74) *Attorney, Agent, or Firm* — Schwegman Lundberg & Woessner, P.A.

(57) ABSTRACT

Video processing for motor task analysis is described. In various examples, a video of at least part of a person or animal carrying out a motor task, such as placing the forefinger on the nose, is input to a trained machine learning system to classify the motor task into one of a plurality of classes. In an example, motion descriptors such as optical flow are computed from pairs of frames of the video and the motion descriptors are input to the machine learning system. For example, during training the machine learning system identifies time-dependent and/or location-dependent acceleration or velocity features which discriminate between the classes of the motor task. In examples, the trained machine learning system computes, from the motion descriptors, the location dependent acceleration or velocity features which it has learned as being good discriminators. In various (Continued)

examples, a feature is computed using sub-volumes of the video.

19 Claims, 9 Drawing Sheets

(51) Int. Cl.
*G16H 50/20* (2018.01)
*G06F 19/00* (2018.01)
*G06N 5/02* (2006.01)
*G06N 99/00* (2010.01)
*G06K 9/62* (2006.01)
*G06N 5/00* (2006.01)
*G06T 7/20* (2017.01)

(52) U.S. Cl.
CPC ....... *G06K 9/00342* (2013.01); *G06K 9/6267* (2013.01); *G06K 9/6278* (2013.01); *G06N 5/00* (2013.01); *G06N 5/025* (2013.01); *G06N 99/005* (2013.01); *G06T 7/20* (2013.01); *G16H 50/20* (2018.01); *G06F 19/3481* (2013.01)

(58) Field of Classification Search
CPC ............ G06K 9/00389; G06K 9/00342; A61B 5/1118; A63B 24/0062; A63B 24/0075; A63B 24/0003; A63B 24/0006; A63B 24/0059; A63B 2024/0012; A63B 2024/0065; A63B 2024/0096; A63B 2024/0009; A63B 2024/0068; A63B 2024/0015; A63B 2244/20; A63B 2243/007; A63B 2243/0025; A63B 69/36; A63B 69/38; A63B 69/0002; A63B 69/004; A63B 69/00; A63B 2071/0647; A63B 2102/18; A63B 2102/32; A63B 23/1209; A63B 21/00178; A63B 21/4027; A63B 71/06; A63B 2022/0094; A63B 26/003
See application file for complete search history.

(56) References Cited

U.S. PATENT DOCUMENTS

| | | | |
|---|---|---|---|
| 2002/0087269 A1* | 7/2002 | Sasaki | B60R 1/00 701/301 |
| 2004/0193413 A1* | 9/2004 | Wilson | G06F 3/017 704/243 |
| 2006/0018516 A1* | 1/2006 | Masoud | G06K 9/00342 382/115 |
| 2006/0098845 A1* | 5/2006 | Sotriropoulos | G06K 9/00335 382/107 |
| 2007/0177792 A1* | 8/2007 | Ma | G06K 9/00348 382/155 |
| 2009/0024050 A1 | 1/2009 | Jung et al. | |
| 2011/0044501 A1* | 2/2011 | Tu | A63F 13/06 382/103 |
| 2011/0182469 A1* | 7/2011 | Ji | G06K 9/4628 382/103 |
| 2011/0263946 A1 | 10/2011 | El Kaliouby et al. | |
| 2012/0164613 A1 | 6/2012 | Jung et al. | |
| 2012/0214594 A1* | 8/2012 | Kirovski | A63F 13/06 463/36 |
| 2012/0218177 A1* | 8/2012 | Pang | G06F 3/0346 345/156 |
| 2012/0235903 A1* | 9/2012 | Im | G06F 3/005 345/158 |
| 2013/0041290 A1 | 2/2013 | Kording et al. | |
| 2013/0156297 A1 | 6/2013 | Shotton et al. | |
| 2013/0294651 A1* | 11/2013 | Zhou | G06K 9/00355 382/103 |
| 2014/0024971 A1 | 1/2014 | Bunn et al. | |
| 2014/0119608 A1 | 5/2014 | Lee et al. | |
| 2014/0314269 A1* | 10/2014 | Chen | G06K 9/00335 382/103 |
| 2014/0379292 A1* | 12/2014 | Ara | A61B 5/11 702/141 |
| 2015/0309583 A1* | 10/2015 | Lim | G06F 3/017 345/156 |
| 2016/0027325 A1* | 1/2016 | Malhotra | G06F 19/3481 434/252 |
| 2016/0148391 A1* | 5/2016 | Chua | G06K 9/00342 382/103 |

OTHER PUBLICATIONS

Zhu, Guangyu, Changsheng Xu, Wen Gao, and Qingming Huang. "Action recognition in broadcast tennis video using optical flow and support vector machine." In Computer Vision in Human-Computer Interaction, pp. 89-98. Springer Berlin Heidelberg, 2006.*

Ke, Yan, Rahul Sukthankar, and Martial Hebert. "Efficient visual event detection using volumetric features." In Computer Vision, 2005. ICCV 2005. Tenth IEEE International Conference on, vol. 1, pp. 166-173. IEEE, 2005.*

Ribeiro, Pedro Canotilho, and José Santos-Victor. "Human activity recognition from video: modeling, feature selection and classification architecture." In Proceedings of International Workshop on Human Activity Recognition and Modelling, pp. 61-78. 2005.*

Schwarz, Loren Arthur, Artashes Mkhitaryan, Diana Mateus, and Nassir Navab. "Human skeleton tracking from depth data using geodesic distances and optical flow." Image and Vision Computing 30, No. 3 (2012): 217-226.*

Efros, Alexei, Alexander C. Berg, Greg Mori, and Jitendra Malik. "Recognizing action at a distance." In Computer Vision, 2003. Proceedings. Ninth IEEE International Conference on, pp. 726-733. IEEE, 2003.*

Nakata, Toru. "Recognizing human activities in video by multi-resolutional optical flows." In Intelligent Robots and Systems, 2006 IEEE/RSJ International Conference on, pp. 1793-1798. IEEE, 2006.*

Holte, Michael B., Thomas B. Moeslund, and Preben Fihl. "View-invariant gesture recognition using 3D optical flow and harmonic motion context." Computer Vision and Image Understanding 114, No. 12 (2010): 1353-1361.*

Aved, Alexander J., and Kien A. Hua. "A general framework for managing and processing live video data with privacy protection." Multimedia systems 18, No. 2 (2012): 123-143.*

Brand, Matthew, and Vera Kettnaker. "Discovery and segmentation of activities in video." IEEE Transactions on Pattern Analysis and Machine Intelligence 22, No. 8 (2000): 844-851.*

Hoai, Minh, Zhen-Zhong Lan, and Fernando De la Torre. "Joint segmentation and classification of human actions in video." In Computer Vision and Pattern Recognition (CVPR), 2011 IEEE Conference on, pp. 3265-3272. IEEE, 2011.*

Lv, Fengjun, and Ramakant Nevatia. "Recognition and segmentation of 3-d human action using hmm and multi-class adaboost." In European conference on computer vision, pp. 359-372. Springer Berlin Heidelberg, 2006.*

Lin, Ting-Yang, Chung-Hung Hsieh, and Jiann-Der Lee. "A kinect-based system for physical rehabilitation: Utilizing tai chi exercises to improve movement disorders in patients with balance ability." In Modelling Symposium (AMS), 2013 7th Asia, pp. 149-153. IEEE, 2013.* de Morais, Wagner O., and Nicholas Wickström. "A serious computer game to assist Tai Chi training for the elderly." In Serious Games and Applications for Health (SeGAH), 2011 IEEE 1st International Conference on, pp. 1-8. IEEE, 2011.*

Roy, Anil K., Yash Soni, and Sonali Dubey. "Enhancing effectiveness of motor rehabilitation using kinect motion sensing technology." In Global Humanitarian Technology Conference: South Asia Satellite (GHTC-SAS), 2013 IEEE, pp. 298-304. IEEE, 2013.*

Çeliktutan, Oya, Ceyhun Burak Akgul, Christian Wolf, and Bülent Sankur. "Graph-based analysis of physical exercise actions." In

(56) References Cited

OTHER PUBLICATIONS

Proceedings of the 1st ACM international workshop on Multimedia indexing and information retrieval for healthcare, pp. 23-32. ACM, 2013.*
Behrens, et al., "Using Perceptive Computing in Multiple Sclerosis—the Short Maximum Speed Walk test", In Journal of NeuroEngineering and Rehabilitation, vol. 11, No. 1, May 27, 2014, 10 pages.
Azrour, et al., "Using GAit Measuring System (GAIMS) to discriminate patients with multiple sclerosis from healthy person", In Workshop on measurement: Challenges and Opportunities, Nov. 7, 2013, 1 page.
Lozano-Quilis, et al., "Virtual Reality System for Multiple Sclerosis Rehabilitation using KINECT", In Proceedings of the 7th International Conference on Pervasive Computing Technologies for Healthcare, May 5, 2013, 4 pages.
Pierard, et al., "Diagnosing Multiple Sclerosis with a Gait Measuring System, an Analysis of the Motor Fatigue, and Machine Learning", In Joint ACTRIMS-ECTRIMS Meeting, Sep. 10, 2014, 1 page.
Bradski, Gary, "The OpenCV Library", In Dr. Dobb's Journal of Software Tools vol. 25, No. 11, Nov. 1, 2000, 6 pages.
Breiman, Leo, "Random Forests", In Machine Learning, vol. 45, Issue 1, Oct. 1, 2001, pp. 5-32.
Criminisi, et al., "Decision Forests in Computer Vision and Medical Image Analysis", In Publication of Springer, Feb. 7, 2013, 3 pages.
Criminisi, et al., "GeoS: Geodesic Image Segmentation", In Proceedings of 10th European Conference on Computer Vision, Oct. 12, 2008, pp. 99-112.
Datta, et al., "A Comprehensive Approach to the Segmentation of Multichannel Three-Dimensional MR Brain Images in Multiple Sclerosis", In Proceedings of NeuroImage: Clinical, vol. 2, Jan. 2013, pp. 184-196.
Geremia, et al., "Spatial Decision Forests for MS Lesion Segmentation in Multi-Channel Magnetic Resonance Images", In Proceedings of Neuroimage, vol. 57, Issue 2, Jul. 15, 2011, 46 pages.
Goodkin, et al., "Inter- and Intrarater Scoring Agreement using Grades 1.0 to 3.5 of the Kurtzke Expanded Disability Scale Status (EDSS)", In Proceedings of Neurology, vol. 42, Issue 4, Apr. 1992, 4 pages.
Kurtzke, John F., "Rating Neurologic Impairment in Multiple Sclerosis: An Expanded Disability Status Scale (EDSS)", In Proceedings of Neurology, vol. 33, No. 11, Nov. 1983, pp. 1444-1452.
Laptev, et al., "Learning Realistic Human Actions from Movies", In IEEE Conference on Computer Vision and Pattern Recognition, Jun. 23, 2008, 8 pages.

Noseworthy, et al., "Interrater Variability with the Expanded Disability Status Scale (EDSS) and Functional Systems (FS) in a Multiple Sclerosis Clinical Trial", In Proceedings of Neurology, vol. 40, No. 06, Jun. 1990, 6 pages.
Pfueller, et al., "Kinect-Based Analysis of Posture, Gait and Coordination in Multiple Sclerosis Patients", In Proceedings of Neurology, vol. 80, Feb. 12, 2013, 2 pages.
Shotton, et al., "Efficient Human Pose Estimation from Single Depth Images", In IEEE Transactions on Pattern Analysis and Machine Intelligence, vol. 35, No. 12, Dec. 2013, pp. 2821-2840.
Vapnik, V. N., "The Nature of Statistical Learning Theory", In Publication of Springer-Verlag, Sep. 3, 2014, 2 pages.
Zach, et al., "A Duality based Approach for Realtime TV-L1 Optical Flow", In Proceedings of the 29th DAGM Conference on Pattern Recognition, Sep. 12, 2007, 10 pages.
Kontschieder, et al "Quantifying progression of multiple sclerosis via classification of depth videos" Medical Image Computing and Computer-Assisted Intervention—MICCAI 17th international conference, Boston, MA, USA, Sep. 14-18, 2014 Proceedings, Part II, Lecture notes in computer science vol. 8874, 2014, pp. 429-437.
"International Search Report and Written Opinion Issued in PCT Application No. PCT/US2015/048753", dated Nov. 19, 2015, 15 Pages.
Poppe, et al., "A Survey on Vision-Based Human Action Recognition", In Journal of Image and Vision Computing, vol. 28, Issue 6, Jun. 1, 2010, 15 Pages.
Poudel, et al., "A Unified Framework for 3D Hand Tracking", In Proceedings of the 3rd International Conference on Grid and Cooperative Computing, Jul. 29, 2013, 11 Pages.
Rani, et al., "Human Action Recognition Using a Hybrid NTLD Classifier", In Proceedings of 7th International Conference on Advanced Video and Signal Based Surveillance, Aug. 29, 2010, pp. 262-269.
Wei-Chia, et al., "Human Upper-Body Motion Capturing Using Kinect", In Proceedings of International Conference on Audio, Language and Image Processing, Jul. 7, 2014, pp. 245-250.
Weinland, et al., "A Survey of Vision-Based Methods for Action representation, Segmentation and Recognition", <<http://hal.inria.fr/docs/00/45/96/53/PDF/RR-7212.pdf>>, Feb. 24, 2010, 57 Pages.
"Motion Detection", <<http://en.wikipedia.org/w/index.php?title=Motion_detection&oldid=621654803>>, Aug. 17, 2014, 4 Pages.
"Motion Field", <<http://en.wikipedia.org/wiki/Motion_field#Relation_to_optical_flow>>, Aug. 2, 2011, 3 Pages.
"Optical Flow", <<http://en.wikipedia.org/w/index.php?title=Optical_flow&oldid=540641648>>, Feb. 26, 2013, 5 Pages.

* cited by examiner

VIDEO PROCESSING FOR MOTOR TASK ANALYSIS

CROSS-REFERENCE TO RELATED APPLICATION

This non-provisional utility application claims priority to US provisional application Ser. No. 62/048,132 entitled "VIDEO PROCESSING FOR MOTOR TASK ANALYSIS" and filed on Sep. 9, 2014, which is incorporated herein in its entirety by reference.

STATEMENT OF JOINT RESEARCH AGREEMENT

The invention claimed herein arose from joint research under a joint research agreement between Microsoft Research Limited and Novartis Pharma AG.

BACKGROUND

Performance of motor tasks such as lifting an arm, standing upright, raising a leg and others typically vary considerably between individuals. For example, depending on body structure, body weight, and other factors such as the expertise and skill of the individual, experience, strength, and physical ability. Existing methods of analysis of motor task performance typically involve manual observation and as such are subjective and open to variation depending on the skill of the observer in making the analysis.

The embodiments described below are not limited to implementations which solve any or all of the disadvantages of known motor task analysis systems.

SUMMARY

The following presents a simplified summary of the disclosure in order to provide a basic understanding to the reader. This summary is not an extensive overview of the disclosure and it does not identify key/critical elements or delineate the scope of the specification. Its sole purpose is to present a selection of concepts disclosed herein in a simplified form as a prelude to the more detailed description that is presented later.

Video processing for motor task analysis is described. In various examples, a video of at least part of a person or animal carrying out a motor task, such as placing the forefinger on the nose, is input to a trained machine learning system to classify the motor task into one of a plurality of classes. In an example, motion descriptors such as optical flow are computed from pairs of frames of the video and the motion descriptors are input to the machine learning system. For example, during training the machine learning system identifies time-dependent and/or location-dependent acceleration or velocity features which discriminate between the classes of the motor task. In examples, the trained machine learning system computes, from the motion descriptors, the location dependent acceleration or velocity features which it has learned as being good discriminators. In various examples, a feature is computed using sub-volumes of the video.

Many of the attendant features will be more readily appreciated as the same becomes better understood by reference to the following detailed description considered in connection with the accompanying drawings.

DESCRIPTION OF THE DRAWINGS

The present description will be better understood from the following detailed description read in light of the accompanying drawings, wherein.

Like reference numerals are used to designate like parts in the accompanying drawings.

DETAILED DESCRIPTION

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

Figure 1:
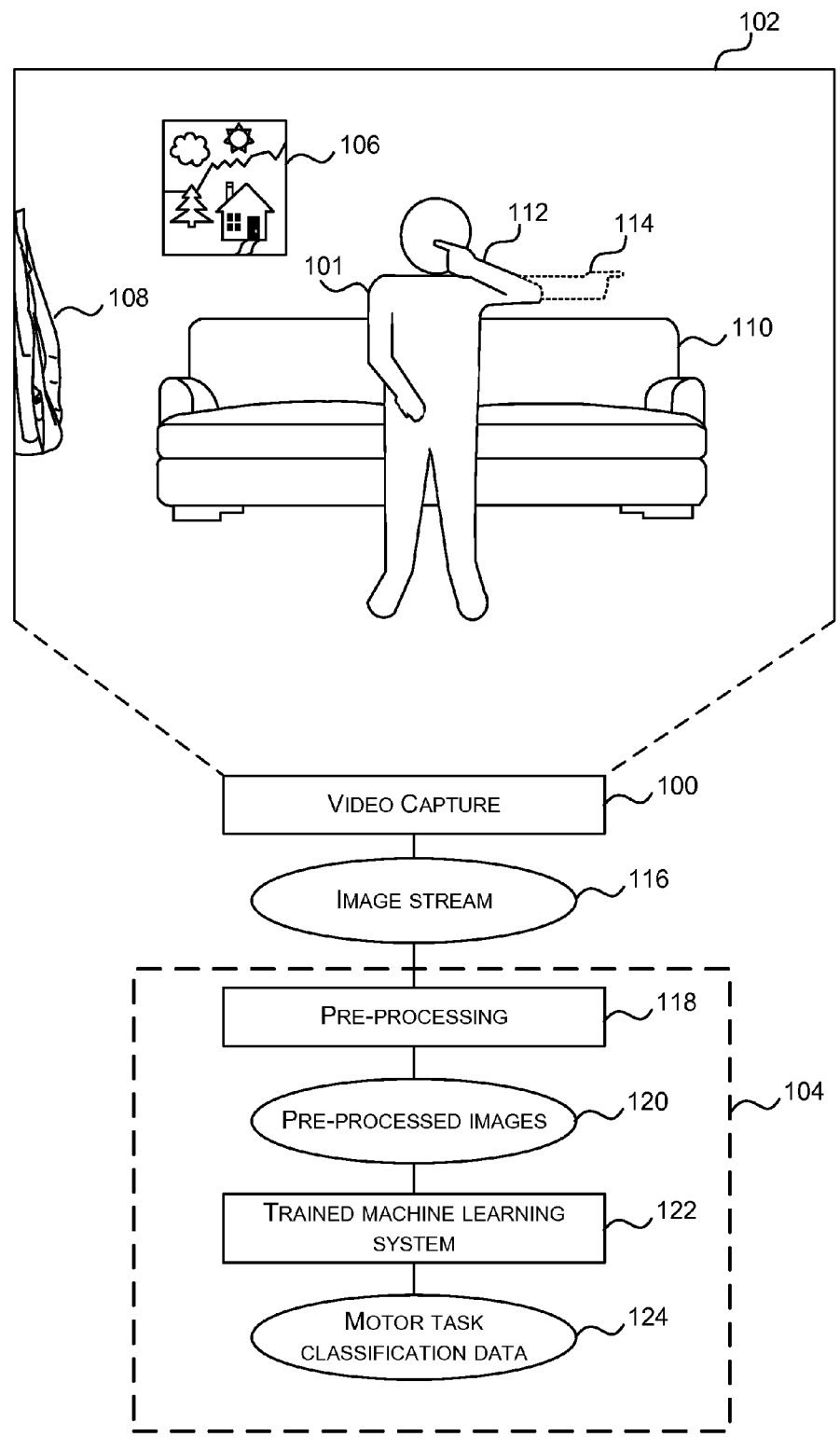
FIG. 1 is a schematic diagram of video capture of a person carrying out a motor task, and showing processing of the video to analyze the motor task.

FIG. 1 is a schematic diagram of a person 101 performing a motor task such as placing a forefinger on the nose (as indicated by arm position 112) after starting from a position where the arm is outstretched horizontally (as indicated by arm position 114). This is only one example of a motor task and more are given below with reference to FIG. 2.

Analyzing motor tasks has previously been achieved manually (e.g. by visual observation) which is subject to variability such as biases of the observer, observer experience level, and the observer environment. In various examples described below, videos of motor tasks are processed to analyze the motor tasks. For example, to classify the motor tasks into two or more classes such as good, medium, weak (for example, to indicate performance level of the motor task). By using an automated, video processing system as described herein it is possible to obtain unbiased, accurate ratings/classifications in a fast and practical manner.

A video capture device 100 captures video of a person 101 carrying out a motor task in an environment, which in the example of FIG. 1 is a room with a picture 106 on the wall, a couch 110, and a garment 108 hanging on the wall. However, this is an example only and other environments may be used. The video capture device 100 may be mounted on the wall facing the user or may be supported in another manner such as on a computing device, table or other structure. The video capture device 100 is described in more detail with reference to FIG. 2. It captures an image stream 116 comprising a plurality of frames captured at a frame rate such as 30 frames per second or more. Other frame rates can be used depending on the type of motor task and video capture equipment. Videos of people are captured with appropriate consent and the video material is preferably stored in a secure, private manner.

The captured frames may be input to a computing device 104 which may be integral with the video capture device 100 or may be connected to the video capture device using wireless communications, wired connection or in other ways. The computing device 104 may be in the cloud, provided as a cloud service. The example of FIG. 1 shows a single computing device 104. However, it is also possible to use a plurality of distributed computing devices which together provide the functionality.

The computing device 104 of FIG. 1 comprises a pre-processing component 118 which pre-processes the video to produce pre-processed images 120. It also comprises a trained machine learning system 122 such as a random decision forest, an ensemble of support vector machines, or other trained machine learning system which outputs motor task classification data 124.

The machine learning system is trained to learn location-dependent, local motion features which are good discriminators of the motor task classes. For example, randomly selected local motion features can be assessed during training and those which perform good discrimination are selected. Location-dependent features are characteristics of one or more sub-volumes of the video. The sequence of frames forming a video can be thought of as forming a volume and a sub-volume is a contiguous region of the larger volume. Characteristics of a sub-volume are location dependent because the sub-volume is at a particular location in time and space of the video. Local motion features are characteristics of one or more sub-volumes related to how image elements within frames of the sub-volume change location between the image frames. For example, the local motion features may relate to velocity or acceleration of image elements. The term acceleration is used here to refer to rate of change of either magnitude of velocity, or rate of change of direction of velocity, or both rate of change of magnitude and direction of velocity. It has been found that location-dependent local motion features can provide effective discriminators for motor task classes as explained in more detail in this document.

Figure 2:
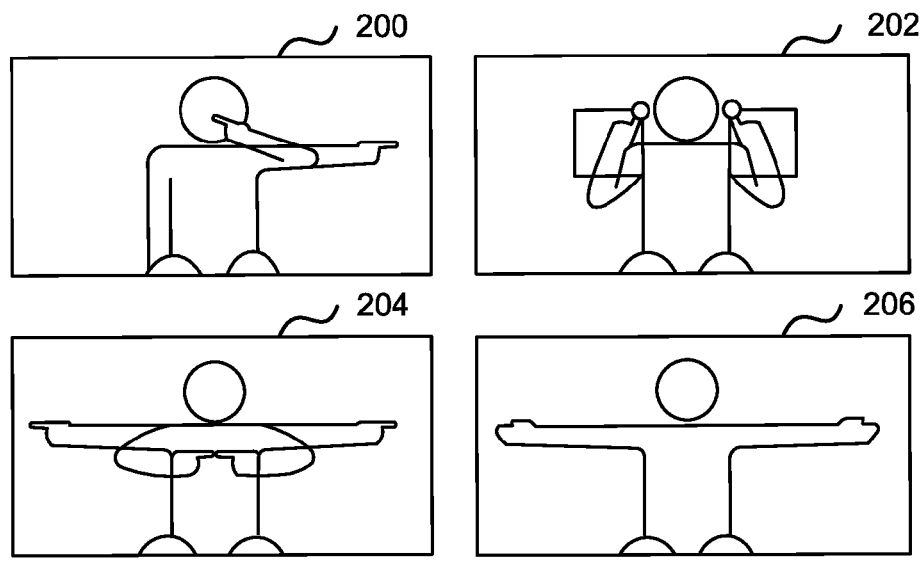
FIG. 2 is a schematic diagram of examples of motor tasks.

FIG. 2 is a schematic diagram of four different types of motor task which may be analysed. A finger to nose task 200 is shown where a person raises one arm to a horizontal position and points the forefinger; the person then moves the arm so as to place the forefinger on the nose. A finger to finger task 204 involves a person raising both arms to horizontal positions with the forefingers pointing away from the body. The person then moves both arms so that the forefingers meet in front of the body. A drawing squares task 202 involves a person drawing equal sized squares in the air; one with each forefinger. A truncal ataxis task 206 involves a person stretching both arms out horizontally away from the body and holding the position. The examples of motor tasks given in FIG. 2 are not an exhaustive list of examples of possible motor tasks but are given to illustrate the technology.

Figure 3:
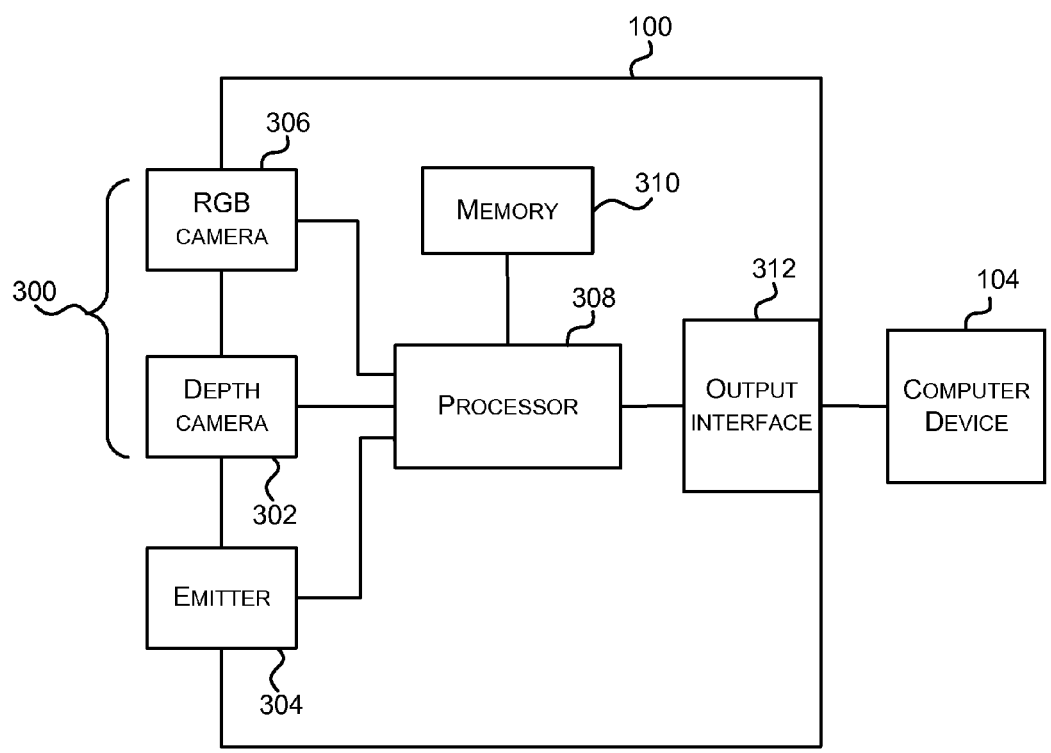
FIG. 3 is a schematic diagram of a capture device which may be used in the scenario of FIG. 1.

Reference is now made to FIG. 3, which illustrates a schematic diagram of an example video capture device 100 that can be used in the camera-based system of FIG. 1. In the example of FIG. 3 the video capture device 100 is configured to capture depth videos (using depth camera 302) as well as color videos (using RGB camera 306). However, this is not essential. It is also possible to capture only color videos, or only depth videos. Where a depth camera 302 is used it can be of any suitable type, for example, time-of-flight, structured light, stereo. The depth camera may use speckle decorrelation in some examples. Where a color video camera is used, facial features or other visual features which may identify a person may be redacted from the color video.

The video capture device 100 comprises at least one imaging sensor 300. In the example shown in FIG. 3, the imaging sensor 300 comprises a depth camera 302 arranged to capture a depth image of a scene. The captured depth image can include a two-dimensional (2-D) area of the captured scene where each image element in the 2-D area represents a depth value such as a length or distance of an object in the captured scene from the depth camera 302.

The capture device can also include an emitter 304 arranged to illuminate the scene in such a manner that depth information can be ascertained by the depth camera 302. For example, in the case that the depth camera 302 is an infra-red (IR) time-of-flight camera, the emitter 304 emits IR light onto the scene, and the depth camera 302 is arranged to detect backscattered light from the surface of one or more targets and objects in the scene. In some examples, pulsed infrared light can be emitted from the emitter 304 such that the time between an outgoing light pulse and a corresponding incoming light pulse can be detected by the depth camera and measured and used to determine a physical distance from the video capture device 100 to a position on the targets or objects in the scene. Additionally, in some examples, the phase of the outgoing light wave from the emitter 304 can be compared to the phase of the incoming light wave at the depth camera 302 to determine a phase shift. The phase shift can then be used to determine a physical distance from the capture device 100 to a position on the targets or objects. In a further example, time-of-flight analysis can be used to indirectly determine a physical distance from the capture device 100 to a position on the targets or objects by analyzing the intensity of the reflected beam of light over time via various techniques including, for example, shuttered light pulse imaging.

In another example, the capture device 100 can use structured light to capture depth information. In such a technique, patterned light (e.g., light displayed as a known pattern such as grid pattern or a stripe pattern) can be projected onto the scene using the emitter 304. Upon striking the surface of one or more targets or objects in the scene, the pattern becomes deformed. Such a deformation of the pattern can be captured by the depth camera 302 and then be analyzed to determine a physical distance from the capture device 100 to a position on the targets or objects in the scene.

In another example, the depth camera 302 can be in the form of two or more physically separated cameras that view a scene from different angles, such that visual stereo data is obtained that can be resolved to generate depth information. In this case the emitter 304 can be used to illuminate the scene or can be omitted.

In some examples, in addition to or instead of, the depth camera 302, the capture device 100 can comprise an RGB camera 306. The RGB camera 306 is arranged to capture sequences of images of the scene at visible light frequencies, and can hence provide images that can be used to augment the depth images. In some examples depth may be computed from the RGB images without the need for a depth camera 306.

For example, the RGB images may be captured without the use of a depth camera, and depth may be computed from the RGB images to provide data that may be used in a similar fashion to the depth images.

The capture device 306 shown in FIG. 3 further comprises at least one processor 308, which is in communication with the imaging sensor 300 (i.e. depth camera 302 and RGB camera 306 in the example of FIG. 3) and the emitter 304. The processor 308 can be a general purpose microprocessor, or a specialized signal/image processor. The processor 308 is arranged to execute instructions to control the imaging sensor 300 and emitter 304 to capture depth videos and/or RGB videos. The processor 308 can also optionally be arranged to perform processing on these videos, as outlined in more detail hereinafter.

The capture device 306 shown in FIG. 3 further includes a memory 310 arranged to store instructions for execution by the processor 308, videos or frames of videos captured by the depth camera 302 or RGB camera 306, or any other suitable information, images, or the like. In some examples, the memory 310 can include random access memory (RAM), read only memory (ROM), cache, Flash memory, a hard disk, or any other suitable storage component. The memory 310 can be a separate component in communication with the processor 308 or integrated into the processor 308.

The capture device 100 also comprises an output interface 312 in communication with the processor 308 and is arranged to provide data to the computing device 104 via a communication link. The communication link can be, for example, a wired connection (such as USB™, Firewire™, Ethernet™ or similar) and/or a wireless connection (such as WiFi™, Bluetooth™ or similar). In other examples, the output interface 312 can interface with one or more communication networks (such as the internet) and provide data to the computing device 104 via these networks.

Figure 4:
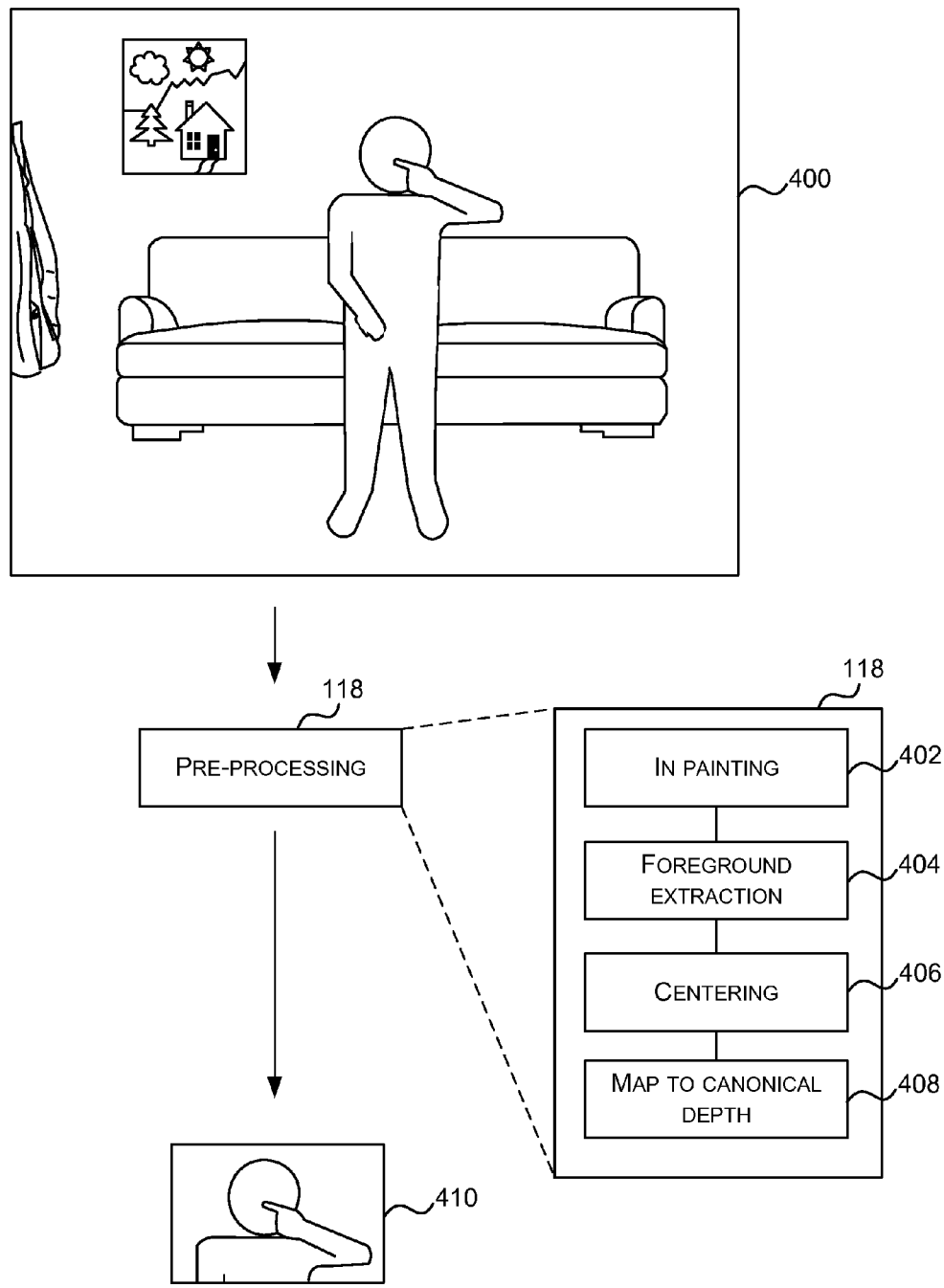
FIG. 4 is a schematic diagram of a frame of the video of FIG. 1 and the result of pre-processing the frame, as well as a pre-processing apparatus.

FIG. 4 is a schematic diagram of a frame 400 of the video of FIG. 1 and the result 410 of pre-processing the frame, as well as a pre-processing apparatus 118. The frame of the video 400 depicts the person slightly off center in this example and at an arbitrary depth from the capture device. The preprocessing apparatus 118 optionally carries out inpainting 402, carries out foreground extraction 404, centering 406 and, in the case depth information is available, maps the foreground to a canonical depth. In this way comparisons between frames of the pre-processed video can be made more simply than if pre-processing did not occur. Inpainting 402 is used where the foreground comprises image elements with missing or erroneous depth values, for example due to noise. This is particularly useful where a depth video camera is used. Inpainting may comprise filling in missing image element values with values calculated on the basis of nearest neighbors of the missing image element, or in other well known ways.

Foreground extraction 404 may be carried out using depth data (in the case depth data is available), for example, using a Gaussian model of depths followed by a geodesic refinement stage. A Gaussian model of depths may comprise a Gaussian mixture model fitted to a histogram of depths observed in a frame. In an example, the first Gaussian mode is taken as corresponding to the foreground. However, other modes or combinations of modes may be used. A geodesic refinement stage may comprise using the image elements that have depth values falling in the most frequent depth range as a seed region and computing geodesic distances of each other image element from the seed region. The geodesic distances may then be used to refine the foreground region using thresholding.

In the case that color videos are used, foreground extraction 404 may be achieved by using color data, by identifying edges in the image, or in other ways.

The centering process 406 may comprise using template-matching to detect a head or other specified body part of the person depicted in the frame. Once detected this body part may be centered in the pre-processed image 410 and scaled or mapped 408 to a canonical depth (in the case that depth frames are involved). In other examples the centering process comprises computing a center of mass of the foreground region and aligning the center of mass with a center of the pre-processed image. In the case that a color video is used the body part is scaled to a specified size rather than mapping to a canonical depth.

A mentioned above, a machine learning system is trained to find location-dependent local motion features which are good discriminators of the motor task classes. The machine learning system is trained using labeled videos 500 of motor tasks. The labels indicate which class the depicted motor task falls into. The labels may be assigned by human judges for example. The labeled videos may be of different lengths. The labeled videos are pre-processed using preprocessing apparatus 118 described above to produce training data 502. Motion descriptors are computed 504 from the training data videos and the motion descriptors are used by a trainer 506 to produce a trained machine learning system 508. For example, the trained machine learning system comprises a random decision forest, an ensemble of randomized support vector machines, neural networks, or boosting systems.

The process of computing the motion descriptors 504 may comprise selecting pairs of video frames 510 from one of the videos (from training data 502) and computing motion descriptors indicating magnitude and/or direction of motion (or change in these quantities) of image elements between the pairs of video frames, otherwise known as a "pairwise analysis". A pair of frames may be two consecutive frames. For example, motion descriptors may be computed for each pair of consecutive frames in a training video and input to the trainer. In an example the motion descriptors 504 comprise optical flow values. Optical flow values are vertical and horizontal displacement values of an image element depicting the same scene element in a pair of video frames. Using optical flow values as the motion descriptors has been found to give robust, accurate results. In another example the motion descriptors 504 comprise displacements of body joint positions between pairs of video frames. In another example the motion descriptors 504 comprise displacements of body part centroids between pairs of video frames. In another example the motion descriptors comprise the area of non-overlap between the foreground region of one frame and the foreground region of another frame.

Figure 5:
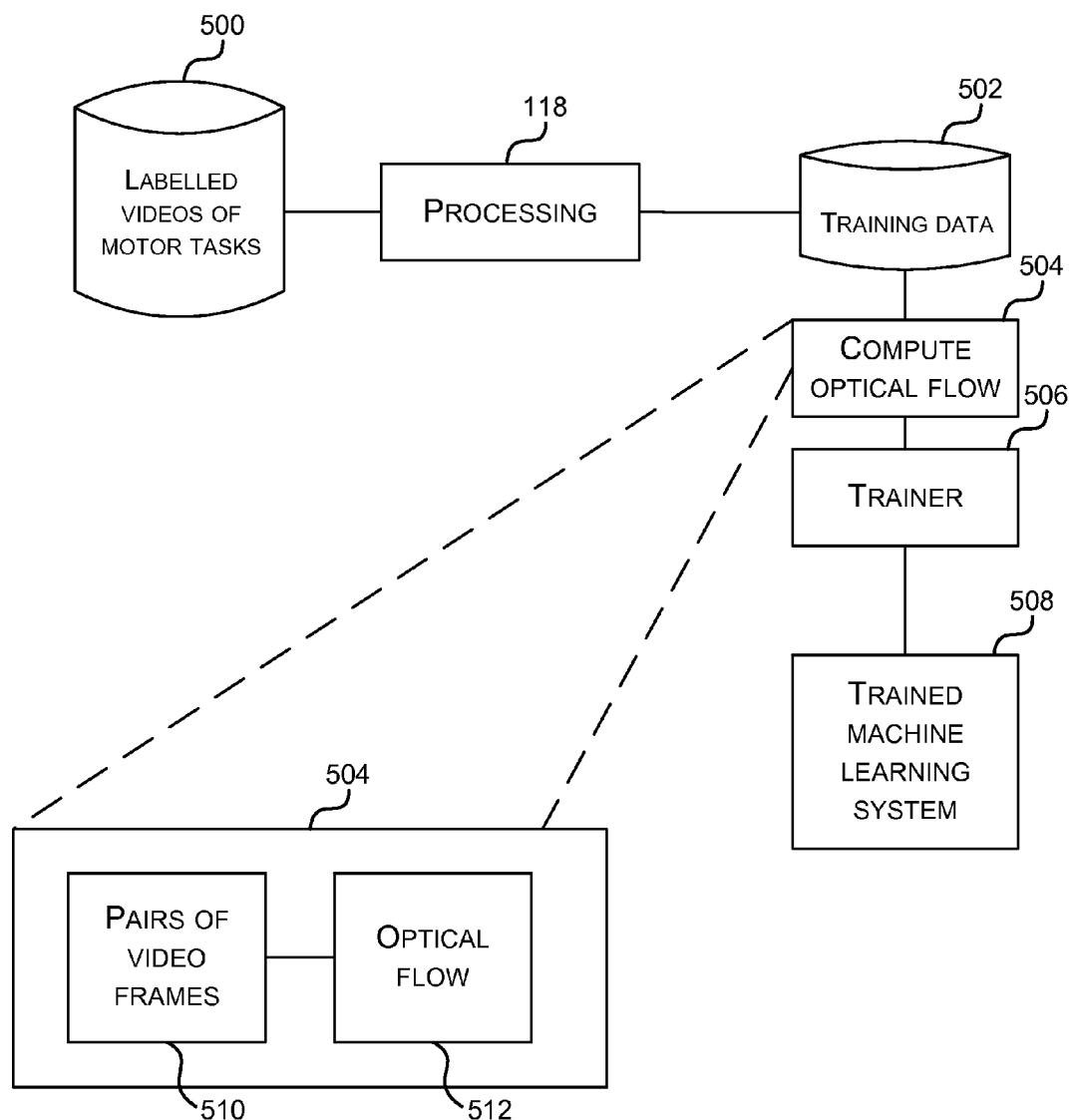
FIG. 5 is a schematic diagram of a system for training a machine learning system to analyze videos of motor tasks.

In the example of FIG. 5 the motion descriptors are computed in advance of input to the trainer. This may also be done at test time. Where the video is long and the image size is large, the number of motion descriptors to be computed is potentially very large, (for all pairs of consecutive frames for example) and so it may be beneficial to pre-compute the motion descriptors. However, it is also possible to compute the motion descriptors as part of the training and/or test phases. The test phase is when the trained machine learning system is used on previously unseen videos (that is, videos not yet presented to the machine learning system).

In some examples, the machine learning system comprises a random decision forest. A random decision forest comprises one or more decision trees each having a root node, a plurality of split nodes and a plurality of leaf nodes.

A video is pushed through trees of a random decision forest from the root to a leaf node in a process whereby a decision is made at each split node. The decision is made according to location-dependent local motion features as described in more detail below. At a split node the video proceeds to the next level of the tree down a branch chosen according to the results of the decision. The random decision forest may use regression or classification as described in more detail below. During training, parameter values (which specify the location-dependent local motion features) are learnt for use at the split nodes and data (labeled videos) is accumulated at the leaf nodes. The labels of the videos accumulated at a leaf node may be stored as a histogram, or in an aggregated manner, such as using a mean, median or mode or by fitting a probability distribution to the histogram and storing statistics describing the probability distribution.

At test time a previously unseen video is input to the system to have one or more motor task classes predicted. This is described with reference to FIG. 8.

Figure 6:
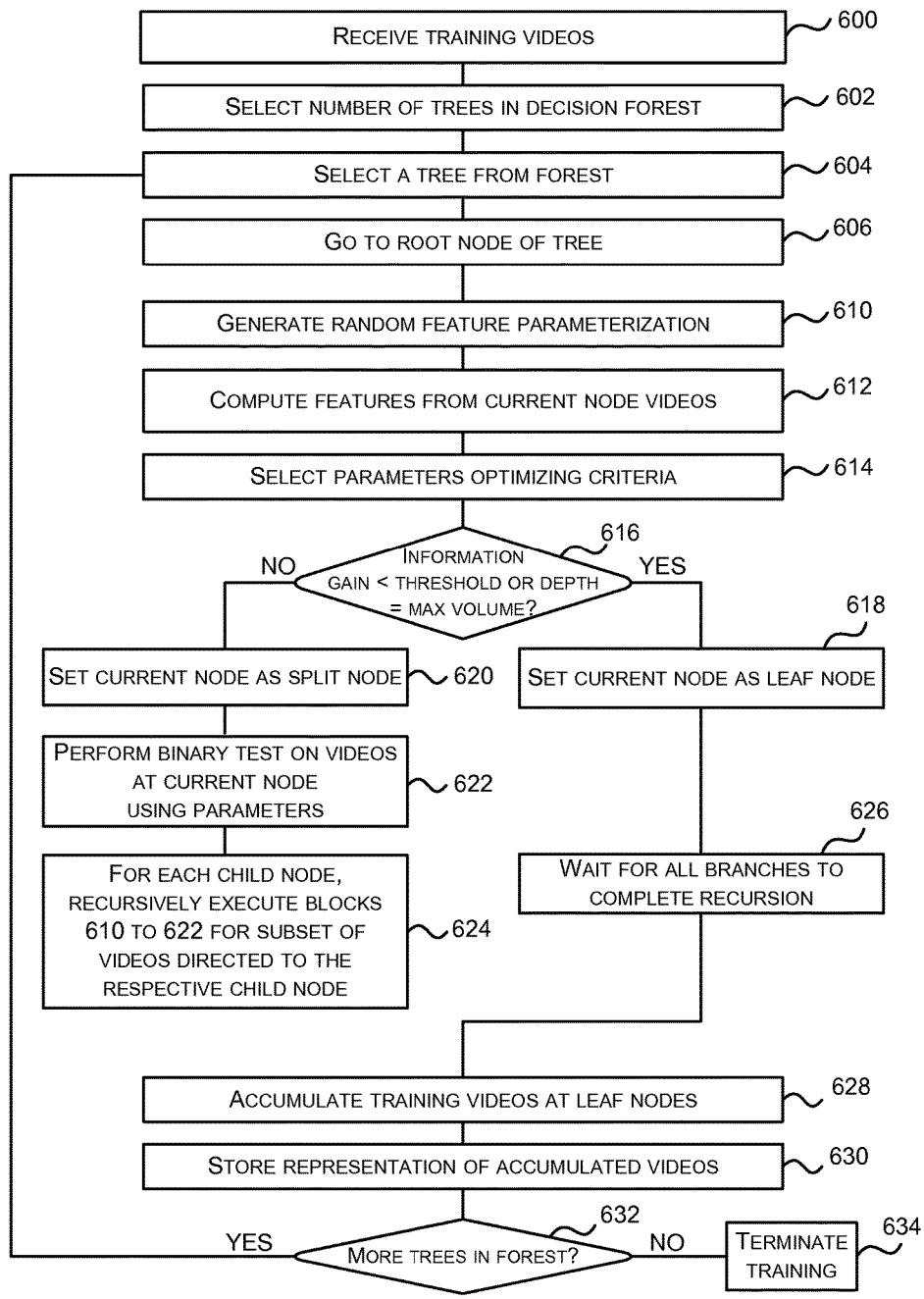
FIG. 6 is a flow diagram of a method of training a random decision forest to classify videos of motor tasks.

Referring to FIG. 6, to train the decision trees, the training set described above is first received 600. The number of decision trees to be used in a random decision forest is selected 602. A random decision forest is a collection of deterministic decision trees. Decision trees can be used in classification or regression algorithms, but can suffer from over-fitting, i.e. poor generalization. However, an ensemble of many randomly trained decision trees (a random forest) yields improved generalization. During the training process, the number of trees is fixed.

Figure 7:
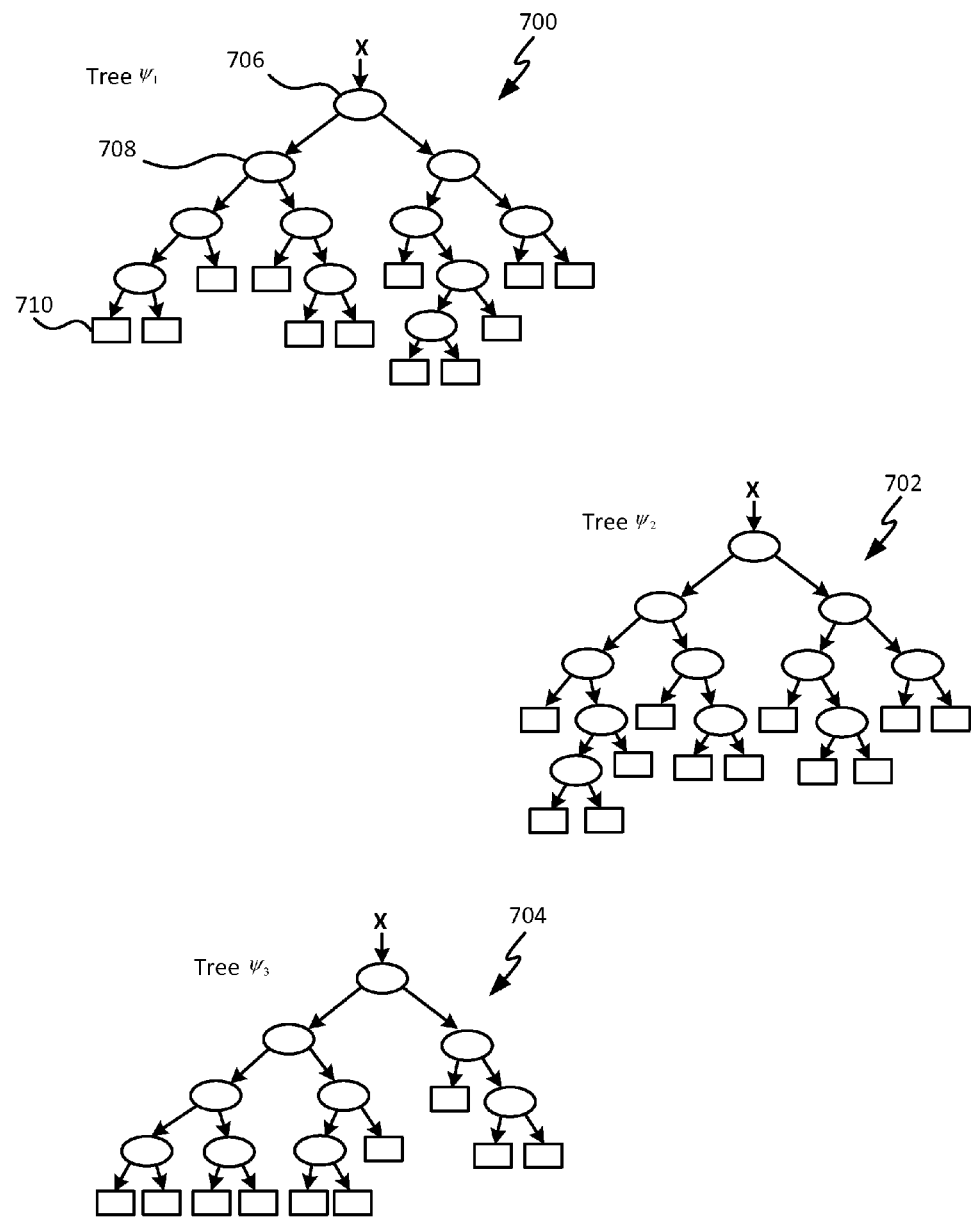
FIG. 7 is a schematic diagram of a random decision forest.

An example random decision forest is shown illustrated in FIG. 7. The illustrative decision forest of FIG. 7 comprises three decision trees: a first tree 700; a second tree 702; and a third tree 704. Each decision tree comprises a root node (e.g. root node 706 of the first decision tree 700), a plurality of internal nodes, called split nodes (e.g. split node 708 of the first decision tree 700), and a plurality of leaf nodes (e.g. leaf node 710 of the first decision tree 700).

A decision tree from the decision forest is selected 604 (e.g. the first decision tree 600) and the root node 606 is selected 606. A random set of test parameters are then generated 610 for use by a binary test performed at the root node as candidate features. In the examples described herein location-dependent local motion features are used. The locations within the video, in 2D within a frame, and and/or in time within the sequence of frames, are selected at random. The features are randomly generated from a plurality of different types of features. For example, the following four types of feature are used which relate to sub-volumes of the video. A sub-volume of the video may be a cuboid selecting a space-time window in the video. A sub-volume may be denoted by symbol B and may be specified by 2D horizontal and vertical image coordinates within a first frame, and 2D horizontal and vertical image coordinates within a second frame, where the number of frames between the first and second frames is specified. For example, $B=(x_1, y_1, x_2, y_2, T'_1, T'_2)$. However, it is not essential to use cuboid shaped sub-volumes. Other 3D shapes of sub-volume may also be used.

A first type of feature is a function of a single sub-volume. An example of a first type of feature is denoted by $f(d_1, B_1)$ which may be expressed in words as a function of a parameter $d_1$ which indicates the type of local motion feature to compute within sub-volume $B_1$. More details about example functions f which may be used are given below.

A second type of feature is a function of two sub-volumes. An example of a second type of feature is denoted by $f(d_1, B_1)+f(d_2, B_2)$ which may be expressed in words as the sum of: a function of a parameter $d_1$ which indicates the type of local motion feature to compute within sub-volume $B_1$, and a function of a parameter $d_1$ which indicates the type of local motion feature to compute within sub-volume $B_1$.

A third type of feature is a function of two sub-volumes. An example of a third type of feature is denoted by $f(d_1, B_1)-f(d_2, B_2)$ which may be expressed in words as the difference of: a function of a parameter $d_1$ which indicates the type of local motion feature to compute within sub-volume $B_1$, and a function of a parameter $d_1$ which indicates the type of local motion feature to compute within sub-volume $B_1$.

A fourth type of feature is a function of two sub-volumes. An example of a fourth type of feature is denoted by $|f(d_1, B_1)-f(d_2, B_2)|$ which may be expressed in words as the absolute difference of: a function of a parameter $d_1$ which indicates the type of local motion feature to compute within sub-volume $B_1$, and a function of a parameter $d_1$ which indicates the type of local motion feature to compute within sub-volume $B_1$.

The function f may be computed by aggregating local motion features such as acceleration or velocity features. An example in which acceleration features are computed is now given.

$$f(d, B) = \frac{1}{(y_2 - y_1)(x_2 - x_1)} \sum_{x'=x_1}^{x_2} \sum_{y'=y_1}^{y_2} \tilde{A}_d^{T(B)}(x', y')$$

Where T(B) is the number of frames of a sub-volume and the symbol $\tilde{A}$ is an estimated acceleration feature (an example of a local motion feature) which may be computed as explained below for each image element location in the sub-volume (or a sub-set of these locations). The above function may be expressed in words as a function f of a given local motion feature type and a given sub-volume is computed as an average of the acceleration features per frame of the subvolume.

The estimated acceleration feature $\tilde{A}$ may be calculated by counting the number of times the rate of change of optical flow vectors changes direction, but ignoring changes of direction where the magnitude of the optical flow vectors is very small (by using a Heaviside step function or a threshold or in other ways).

In another example an estimated velocity feature may be used in place of the estimated acceleration feature above. For example, by counting the number of times the optical flow vectors change direction rather than considering the rate of change of the optical flow vectors.

At step 610 of FIG. 6 a random set of test parameters is generated 610 for use by a binary test performed at a split node as candidate features. In an example, these parameters may include parameters of the sub-volume(s) (i.e. specifying the locations and duration of the sub-volumes to be used), a threshold parameter (for comparing the features against in the binary test), the parameter d which indicates the type of local motion feature to compute (e.g. velocity in the x direction, velocity in the y direction, acceleration in the x direction, acceleration in the y direction), and a variable k selecting one of the four (or other number of) features above.

Then, every combination of test parameter may be applied 612 to each video which has reached the current node. For each combination, criteria (also referred to as objectives) are calculated 614. In an example, the calculated criteria comprise the information gain (also known as the relative entropy). The combination of parameters that optimize the criteria (such as maximizing the information gain is selected 614 and stored at the current node for future use. As an alternative to information gain, other criteria can be used, such as Gini entropy, or the 'two-ing' criterion or others.

It is then determined 616 whether the value for the calculated criteria is less than (or greater than) a threshold. If the value for the calculated criteria is less than the threshold, then this indicates that further expansion of the tree does not provide significant benefit. This gives rise to asymmetrical trees which naturally stop growing when no further nodes are beneficial. In such cases, the current node is set 618 as a leaf node. Similarly, the current depth of the tree is determined (i.e. how many levels of nodes are between the root node and the current node). If this is greater than a predefined maximum value, then the current node is set 618 as a leaf node. Each leaf node has labeled videos which accumulate at that leaf node during the training process as described below.

It is also possible to use another stopping criterion in combination with those already mentioned. For example, to assess the number of videos that reach the node. If there are too few examples (compared with a threshold for example) then the process may be arranged to stop to avoid overfitting. However, it is not essential to use this stopping criterion.

If the value for the calculated criteria is greater than or equal to the threshold, and the tree depth is less than the maximum value, then the current node is set 620 as a split node. As the current node is a split node, it has child nodes, and the process then moves to training these child nodes. Each child node is trained using a subset of the training videos at the current node. The subset of videos sent to a child node is determined using the parameters that optimized the criteria. These parameters are used in the binary test, and the binary test performed 622 on all videos at the current node. The videos that pass the binary test form a first subset sent to a first child node, and the image elements that fail the binary test form a second subset sent to a second child node.

For each of the child nodes, the process as outlined in blocks 610 to 622 of FIG. 6 are recursively executed 624 for the subset of videos directed to the respective child node. In other words, for each child node, new random test parameters are generated 610, applied 612 to the respective subset of videos, parameters optimizing the criteria selected 614, and the type of node (split or leaf) determined 616. If it is a leaf node, then the current branch of recursion ceases. If it is a split node, binary tests are performed 622 to determine further subsets of videos and another branch of recursion starts. Therefore, this process recursively moves through the tree, training each node until leaf nodes are reached at each branch. As leaf nodes are reached, the process waits 626 until the nodes in all branches have been trained. Note that, in other examples, the same functionality can be attained using alternative techniques to recursion.

Once all the nodes in the tree have been trained to determine the parameters for the binary test optimizing the criteria at each split node, and leaf nodes have been selected to terminate each branch, then video labels may be accumulated 628 at the leaf nodes of the tree. A representation of the accumulated video labels may be stored 630 using various different methods.

Once the accumulated labels have been stored it is determined 632 whether more trees are present in the decision forest. If so, then the next tree in the decision forest is selected, and the process repeats. If all the trees in the forest have been trained, and no others remain, then the training process is complete and the process terminates 634.

Therefore, as a result of the training process, one or more decision trees are trained using empirical training videos. Each tree comprises a plurality of split nodes storing optimized test parameters, and leaf nodes storing associated labeled videos or representations of aggregated video labels. Due to the random generation of parameters from a limited subset used at each node, the trees of the forest are distinct (i.e. different) from each other.

The training process may be performed in advance of using the trained prediction system to identify motor task classes in a video. The decision forest and the optimized test parameters may be stored on a storage device for use in identifying motor task classes at a later time.

Figure 8:
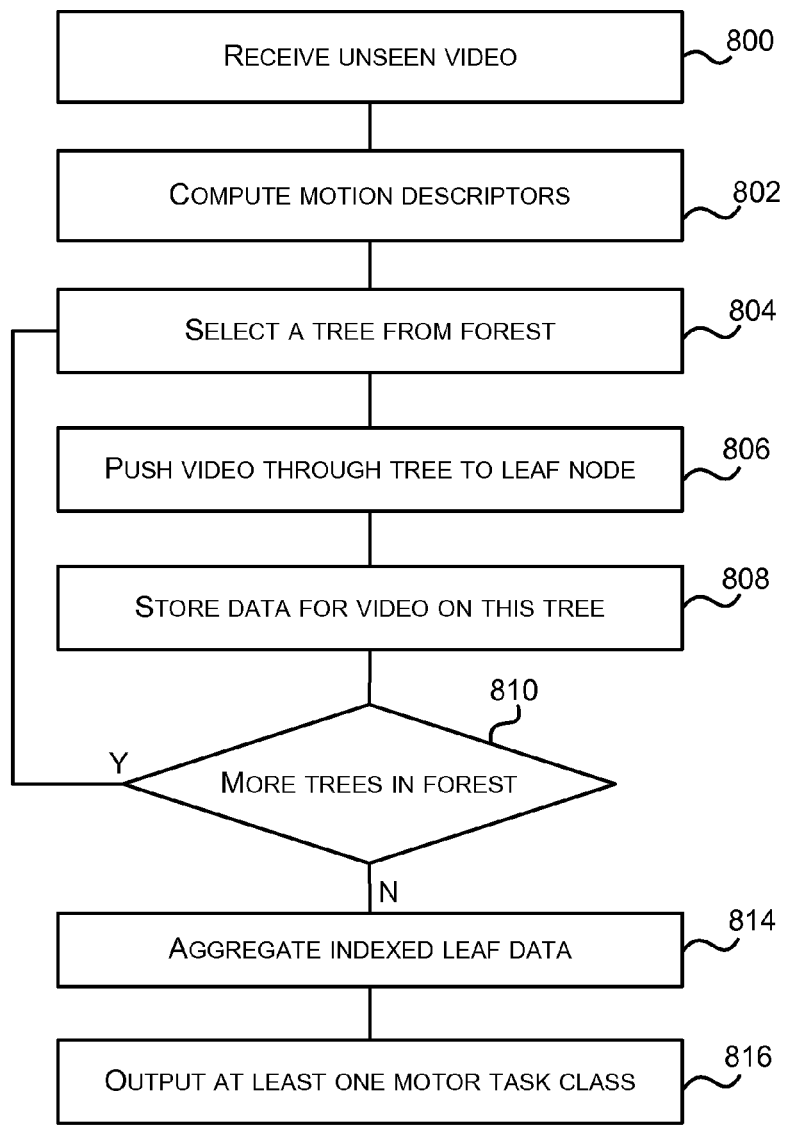
FIG. 8 is a flow diagram of a method of using a trained random decision forest to classify a motor task video.

FIG. 8 illustrates a flowchart of a process for predicting motor task classes in a previously unseen video using a decision forest that has been trained as described above. Firstly, an unseen video is received 800. A video is referred to as 'unseen' to distinguish it from a training video which has the motor task class specified. Note that the unseen video can be pre-processed to an extent, as described above, with reference to FIG. 4.

Optical flow or other motion descriptors are computed 802. A trained decision tree from the decision forest is also selected 804. The selected video is pushed 806 through the selected decision tree (in a manner similar to that described above with reference to FIGS. 6 and 7), such that it is tested against the trained parameters at a node, and then passed to the appropriate child in dependence on the outcome of the test, and the process repeated until the video reaches a leaf node. Once the video reaches a leaf node, the accumulated labels associated with this leaf node are stored 808 for this video.

If it is determined 810 that there are more decision trees in the forest, then a new decision tree is selected 804, the video pushed 806 through the tree and the accumulated labels stored 808. This is repeated until it has been performed for all the decision trees in the forest. Note that the process for pushing a video through the plurality of trees in the decision forest can also be performed in parallel, instead of in sequence as shown in FIG. 8.

The data from the indexed leaf nodes is aggregated 814 by averaging or in other ways. For example, where histograms of class labels are stored at the leaf nodes the histograms from the indexed leaf nodes are combined and used to identify one or more motor tasks associated with the video. The processes outputs 816 at least one motor task class as a result, and is able to output a confidence weighting of the motor task class. This helps any subsequent algorithm assess whether the proposal is good or not. More than one motor class may be output; for example, where there is uncertainty.

In another example the machine learning system comprises an ensemble of support vector machines. A support vector machine is a non-probabilistic, binary classifier which uses hyperplanes in a feature space to achieve the classification.

In an example, a support vector machine is associated with (or replaces) a split node of a random decision forest such as that described above with reference to FIGS. 6 to 8. The support vector machine takes as input the training videos which have reached the respective split node. These input training videos form its feature space and it calculates one or more hyperplanes to make a binary classification of the feature space. In this way support vector machines are used to make the binary decisions rather than assessing information gain or other criteria as described above for random decision trees. In this way the process of FIG. 6 for training a random decision forest can be adapted to train an ensemble of support vector machines by using a support vector machine at each split node. It is also possible to use mixtures of types of split node (random decision split nodes or support vector machine split nodes). The resulting ensemble of support vector machines or mixture of support vector machines/random decision nodes, may be used at test time by modifying the process of FIG. 8. In this way it is possible to use support vector machine technology for a task involving an extremely high and variable number of dimensions in a practical manner. Training is achieved in a practical time scale because each support vector machine receives only the training videos which reach it through the binary tree structure and so its feature space is limited.

Another example in which an ensemble of randomized support vector machines is used is now given. To train the ensemble of randomized support vector machines, a fixed-length feature vector is calculated from each labeled training video. The fixed-length feature vector comprises a plurality of location-dependent local motion features of the video. For example, any combination of one or more of the four features described above in the description about the random decision forest may be used (although other features may be used). By creating a fixed size feature descriptor, such as a vector or list, the resulting system is operable independently of video length. This is achieved without loss of movement characteristics in the videos; in contrast to temporal normalization techniques.

The features in each feature descriptor are selected at random. The feature descriptors define a feature space where the support vector machines perform learning. In an example, an individual support vector machine of the ensemble is trained to find a hyperplane that maximizes the margin between samples of training videos labeled in the different classes. Each of the support vector machines is trained in this way. The resulting ensemble of randomized support vector machines may be used at test time by modifying the process of FIG. 8.

In the examples described above the machine learning system classifies videos of motor tasks into classes or ratings. However, it is also possible for the machine learning system to use regression rather than classification so that continuous valued outputs are obtained from the trained machine learning system, as opposed to discrete class labels. For example, these continuous valued outputs may be numerical values on a motor task assessment scale.

Figure 9:
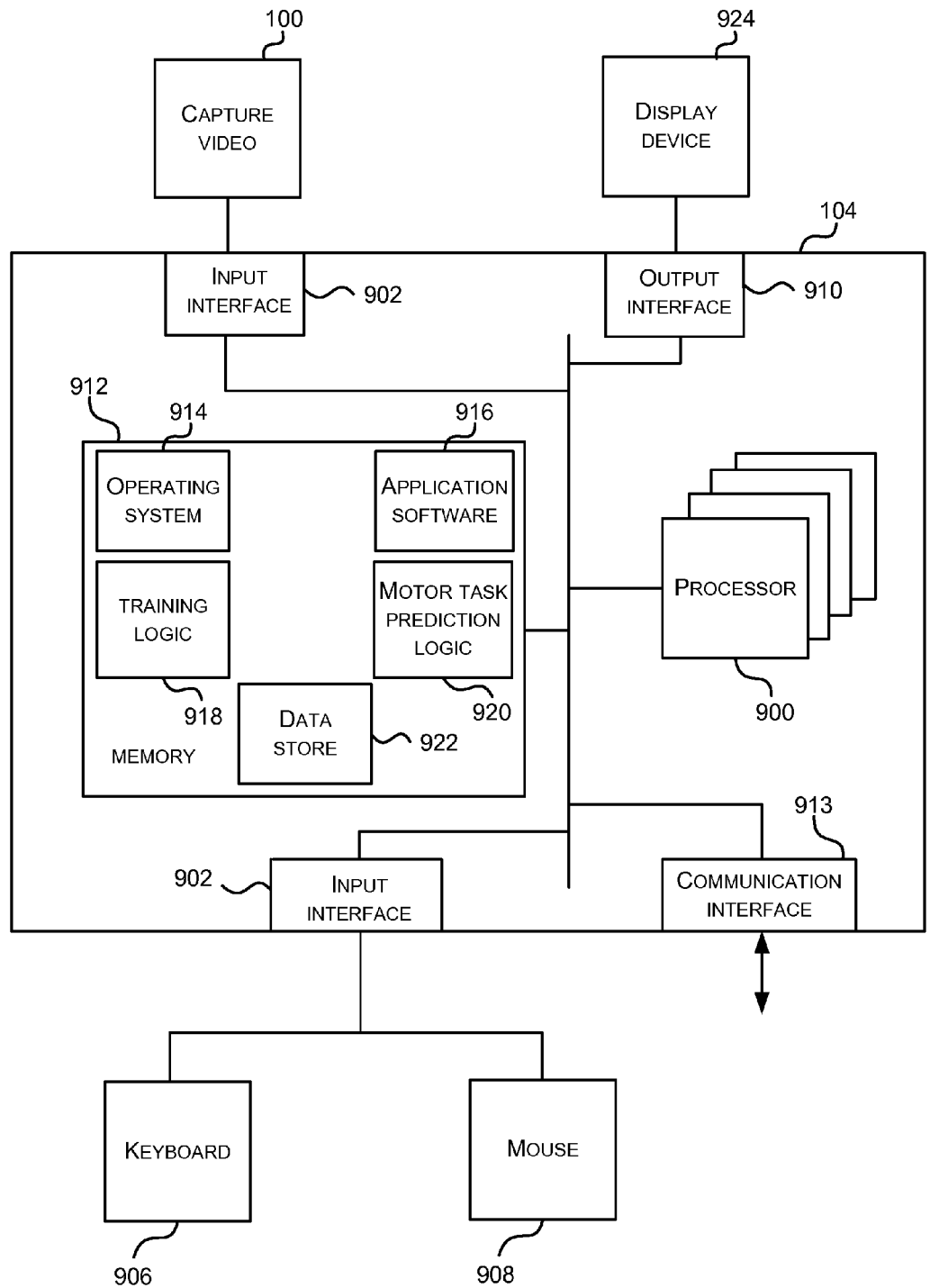
FIG. 9 illustrates an exemplary computing-based device in which embodiments of a video processing system may be implemented.

FIG. 9 illustrates various components of an exemplary computing-based device 104 which may be implemented as any form of a computing and/or electronic device, and in which embodiments of motor task classification systems may be implemented.

Computing-based device 104 comprises one or more processors 900 which may be microprocessors, controllers, graphics processing units, parallel processing units, or any other suitable type of processors for processing computing executable instructions to control the operation of the device in order to predict motor task classes in videos. In some examples, for example where a system on a chip architecture is used, the processors 900 may include one or more fixed function blocks (also referred to as accelerators) which implement a part of the method of motor task classification in hardware (rather than software or firmware).

The computing-based device 104 comprises one or more input interfaces 902 arranged to receive and process input from one or more devices, such as user input devices (e.g. capture device 100, a keyboard 906 and/or a mouse 908). This user input may be used to control software applications executed on the computing device 104.

The computing-based device 104 also comprises an output interface 910 arranged to output display information to a display device 924 which can be separate from or integral to the computing device 104. For example, to display the videos with superimposed motor task classification data. The display information may provide a graphical user interface. In an example, the display device 924 may also act as the user input device if it is a touch sensitive display device. The output interface may also output data to devices other than the display device, e.g. a locally connected printing device.

The computer executable instructions may be provided using any computer-readable media that is accessible by computing based device 104. Computer-readable media may include, for example, computer storage media 1212 such as memory and communications media. Computer storage media 1212, such as memory 912, includes volatile and non-volatile, removable and non-removable media implemented in any method or technology for storage of information such as computer readable instructions, data structures, program modules or other data. Computer storage media includes, but is not limited to, RAM, ROM, EPROM, EEPROM, flash memory or other memory technology, CD-ROM, digital versatile disks (DVD) or other optical storage, magnetic cassettes, magnetic tape, magnetic disk storage or other magnetic storage devices, or any other non-transmission medium that can be used to store information for access by a computing device. In contrast, communication media may embody computer readable instructions, data structures, program modules, or other data in a modulated data signal, such as a carrier wave, or other transport mechanism. As defined herein, computer storage media does not include communication media. Therefore, a computer storage medium should not be interpreted to be a propagating signal per se. Propagated signals may be present in a computer storage media, but propagated signals per se are not examples of computer storage media. Although the computer storage media (memory 912) is shown within the computing-based device 104 it will be appreciated that the storage may be distributed or located remotely and accessed via a network or other communication link (e.g. using communication interface 913).

Platform software comprising an operating system 914 or any other suitable platform software may be provided at the computing device 104 to enable application software 916 to be executed on the device. Other software that can be executed on the computing device 104 includes: training logic 918 (see for example, FIGS. 6-7 and description above); prediction logic 920 (see for example FIG. 8 and description above). A data store 922 is provided to store data such as previously received videos; intermediate function results; tree training parameters, probability distributions, classification labels, regression objectives, classification objectives, and other data.

Any of the input interface 902, output interface 910, display device 924 and the user input devices 906, 908 may comprise NUI technology which enables a user to interact with the computing-based device in a natural manner, free from artificial constraints imposed by input devices such as mice, keyboards, remote controls and the like. Examples of NUI technology that may be provided include but are not limited to those relying on voice and/or speech recognition, touch and/or stylus recognition (touch sensitive displays), gesture recognition both on screen and adjacent to the screen, air gestures, head and eye tracking, voice and speech, vision, touch, gestures, and machine intelligence. Other examples of NUI technology that may be used include intention and goal understanding systems, motion gesture detection systems using depth cameras (such as stereoscopic camera systems, infrared camera systems, rgb camera systems and combinations of these), motion gesture detection using accelerometers/gyroscopes, facial recognition, 3D displays, head, eye and gaze tracking, immersive augmented reality and virtual reality systems and technologies for sensing brain activity using electric field sensing electrodes (EEG and related methods).

In an example there is provided a computer-implemented method comprising:

receiving a video depicting at least part of a person or animal performing a motor task;

inputting the video to a trained machine learning system, having been trained to find location-dependent local motion features of videos which discriminate between a plurality of classes of the motor task;

receiving, from the trained machine learning system, data about which of the plurality of classes the motor task is predicted to belong to.

In this way motor tasks performed by people can be analyzed and assessed in an accurate, repeatable manner which is automated and so objective.

In examples the local motion features comprise velocity or acceleration features. These types of features may be computed accurately and efficiently and may be computed in advance of machine learning training and test phases. This improves the quality of the motor task data obtained from the machine learning system and the speed of obtaining that data.

In examples the above methods comprise calculating, for pairs of frames of the video, motion descriptors, and wherein inputting the video to the trained machine learning system comprises inputting the motion descriptors.

For example the motion descriptors are optical flow values. Where optical flow values are used the resulting system is found to be very robust to noise or errors in the videos.

In some examples the above methods comprise, at the machine learning system, calculating the local motion features using a plurality of the motion descriptors. For example, by taking into account motion descriptors in at least one sub-volume of the video. For example, calculating the local motion features by taking into account motion descriptors in two sub-volumes of the video. For example, calculating the local motion features by taking into account differences between motion descriptors in the sub-volumes of the video. Using sub-volumes of videos in these ways is found particularly effective in discriminating between motor task classes.

Some examples comprise calculating the acceleration features by taking into account frequency of change of direction of rate of change of the optical flow values of a sub-volume of the video. Using a directional acceleration feature is found very effective in discriminating between motor task classes.

Some examples comprise disregarding changes of direction of the rate of change of the optical flow values, where the magnitude of the optical flow is below a threshold. This helps to distinguish between motion due to noise and actual motion of the person.

Some examples comprise pre-processing the video prior to inputting the video to the trained machine learning system, by scaling, centering and carrying out foreground extraction. This simplifies the use of the trained machine learning system at test time and reduces the test time processing duration.

In an example the video is of any length, and the local motion features are calculated in a manner which takes into account the length of the video. This is very useful where the motor tasks exhibit large variability in duration between individuals.

An example comprises training the machine learning system using videos of people performing a motor task, where the videos are labeled with labels indicating which of a plurality of possible classes the motor task belongs to, and where the videos are of different lengths.

The above examples may comprise inputting the video to a trained machine learning system comprising any of: a random decision forest, a jungle of directed acyclic graphs, an ensemble of support vector machines.

Some examples comprise inputting the video to a trained machine learning system comprising an ensemble of support vector machines, each support vector machine being a split node of a binary decision tree. This gives a practical way of using support vector machines despite the high and variable number of dimensions of the video data.

Some examples comprise inputting the video to a trained machine learning system comprising an ensemble of support vector machines, individual ones of the support vector machines having been trained using fixed length feature descriptors comprising randomized location-dependent local motion features computed from labeled training videos. The resulting ensemble of support vector machines may be referred to as a randomized ensemble of support vector machines.

Another example provides a motor-task classifier comprising:

a memory storing a video depicting at least part of a person or animal performing a motor task;

a trained machine learning system, having been trained to find location-dependent local motion features of videos which discriminate between a plurality of classes of the motor task; and a processor arranged to compute motion descriptors from the video, apply the motion descriptors to the trained machine learning system, and to receive in response, data about which of the plurality of classes the motor task is predicted to belong to.

The term 'computer' or 'computing-based device' is used herein to refer to any device with processing capability such that it can execute instructions. Those skilled in the art will realize that such processing capabilities are incorporated into many different devices and therefore the terms 'computer' and 'computing-based device' each include PCs, servers, mobile telephones (including smart phones), tablet computers, set-top boxes, media players, games consoles, personal digital assistants and many other devices.

The methods described herein may be performed by software in machine readable form on a tangible storage medium e.g. in the form of a computer program comprising computer program code means adapted to perform all the steps of any of the methods described herein when the program is run on a computer and where the computer program may be embodied on a computer readable medium. Examples of tangible storage media include computer storage devices comprising computer-readable media such as disks, thumb drives, memory etc. and do not include propagated signals. Propagated signals may be present in a tangible storage media, but propagated signals per se are not examples of tangible storage media. The software can be suitable for execution on a parallel processor or a serial processor such that the method steps may be carried out in any suitable order, or simultaneously.

This acknowledges that software can be a valuable, separately tradable commodity. It is intended to encompass software, which runs on or controls "dumb" or standard hardware, to carry out the desired functions. It is also intended to encompass software which "describes" or defines the configuration of hardware, such as HDL (hardware description language) software, as is used for designing silicon chips, or for configuring universal programmable chips, to carry out desired functions.

Those skilled in the art will realize that storage devices utilized to store program instructions can be distributed across a network. For example, a remote computer may store an example of the process described as software. A local or terminal computer may access the remote computer and download a part or all of the software to run the program. Alternatively, the local computer may download pieces of the software as needed, or execute some software instructions at the local terminal and some at the remote computer (or computer network). Those skilled in the art will also realize that by utilizing conventional techniques known to those skilled in the art that all, or a portion of the software instructions may be carried out by a dedicated circuit, such as a DSP, programmable logic array, or the like.

Any range or device value given herein may be extended or altered without losing the effect sought, as will be apparent to the skilled person.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

It will be understood that the benefits and advantages described above may relate to one embodiment or may relate to several embodiments. The embodiments are not limited to those that solve any or all of the stated problems or those that have any or all of the stated benefits and advantages. It will further be understood that reference to 'an' item refers to one or more of those items.

The steps of the methods described herein may be carried out in any suitable order, or simultaneously where appropriate. Additionally, individual blocks may be deleted from any of the methods without departing from the spirit and scope of the subject matter described herein. Aspects of any of the examples described above may be combined with aspects of any of the other examples described to form further examples without losing the effect sought.

The term 'comprising' is used herein to mean including the method blocks or elements identified, but that such blocks or elements do not comprise an exclusive list and a method or apparatus may contain additional blocks or elements.

The term 'subset' is used herein to refer to a proper subset such that a subset of a set does not comprise all the elements of the set (i.e. at least one of the elements of the set is missing from the subset).

It will be understood that the above description is given by way of example only and that various modifications may be made by those skilled in the art. The above specification, examples and data provide a complete description of the structure and use of exemplary embodiments. Although various embodiments have been described above with a certain degree of particularity, or with reference to one or more individual embodiments, those skilled in the art could make numerous alterations to the disclosed embodiments without departing from the spirit or scope of this specification.

The invention claimed is:

1. A computer-implemented method comprising:
receiving a video depicting at least part of a user performing a motor task;
redacting features from the video which may identify the user;
inputting the video to a trained machine learning system, the trained machine learning system having been trained to detect multiple sequences of location-dependent local motion features of videos which discriminate among a plurality of classes of the motor task; and
receiving, from the trained machine learning system, a label identifying a motor task class of the plurality of classes, the plurality of classes including
an indication of a performance level of the motor task based on at least one of the multiple sequences of location-dependent local motion features in the video detected by the trained machine learning system.

2. A method as claim 1 recites, wherein the local motion features comprise velocity or acceleration features.

3. A method as claim 2 recites further comprising calculating the acceleration features by taking into account frequency of change of direction of rate of change of optical flow values of a sub-volume of the video.

4. A method as claim 3 recites further comprising disregarding changes of direction of the rate of change of the optical flow values, where a magnitude of the optical flow values is below a threshold.

5. A method as claim 1 recites further comprising calculating motion descriptors for pairs of frames of the video, and wherein inputting the video to the trained machine learning system comprises inputting the motion descriptors.

6. A method as claim 5 recites, wherein the motion descriptors include optical flow values.

7. A method as claim 5 recites further comprising, at the machine learning system, calculating the local motion features using a plurality of the motion descriptors.

8. A method as claim 5 recites, wherein the trained machine learning system finds the local motion features by performing a calculation based at least in part on the motion descriptors in at least one sub-volume of the video.

9. A method as claim 5 recites further comprising calculating the local motion features by taking into account differences between motion descriptors in sub-volumes of the video.

10. A method as claim 1 recites further comprising pre-processing the video prior to inputting the video to the trained machine learning system, at least by one or more of scaling, centering, or carrying out foreground extraction.

11. A method as claim 1 recites, wherein:
the video is of any length, and
the trained machine learning system calculates the local motion features based at least in part on the length of the video.

12. A method as claim 1 recites further comprising training the machine learning system using videos of people performing the motor task, where the videos are labeled with labels indicating which of a plurality of possible classes the motor task belongs to, and where the videos are of different lengths.

13. A method as claim 1 recites further comprising inputting the video to a trained machine learning system comprising one or more of: a random decision forest, a jungle of directed acyclic graphs, or an ensemble of support vector machines.

14. A method as claim 1 recites further comprising inputting the video to a trained machine learning system comprising an ensemble of support vector machines, a support vector machine of the ensemble including a split node of a binary decision tree.

15. A method as claim 1 recites further comprising inputting the video to a trained machine learning system comprising an ensemble of support vector machines, individual ones of the support vector machines having been trained using fixed length feature descriptors comprising randomized location-dependent local motion features computed from labeled training videos.

16. A computer storage media storing instructions comprising:
   instructions to receive a video depicting at least part of a person or animal performing a motor task;
   instructions to input the video to a trained machine learning system, having been trained to detect multiple sequences of location-dependent local acceleration features of videos which discriminate among a plurality of classes of the motor task, the local acceleration features calculated by taking into account frequency of change of direction of rate of change of optical flow values of a sub-volume of the video; and
   instructions to receive, from the trained machine learning system a label identifying a motor task class of the plurality of classes, wherein the plurality of classes includes
   an indication of a performance level of the motor task based on at least one of the multiple sequences of location-dependent local motion features in the video detected by the trained machine learning system.

17. A motor-task classifier comprising:
   a trained machine learning system, having been trained to detect multiple sequences of location-dependent local motion features of videos which discriminate among a plurality of classes of a motor task, the training comprising optimizing a criteria based at least in part on a duration of a sub-volume; and
   a processor arranged to:
      compute motion descriptors from a video;
      input the motion descriptors to the trained machine learning system; and
      receive, from the trained machine learning system, a label identifying a motor task class of the plurality of classes, wherein the plurality of classes includes
      an indication of a performance level of the motor task based on at least one of the multiple sequences of location-dependent local motion features in the video detected by the trained machine learning system.

18. A motor-task classifier as claim 17 recites, wherein the local motion features include velocity or acceleration features.

19. A motor-task classifier as claim 17 recites, wherein computing motion descriptors from the video includes calculating motion descriptors for pairs of frames of the video.

* * * * *